(12) United States Patent
Fukada et al.

(10) Patent No.: US 9,850,441 B2
(45) Date of Patent: *Dec. 26, 2017

(54) METHOD FOR BLENDING COALS, AND METHOD FOR PRODUCING COKE

(71) Applicant: JFE STEEL CORPORATION, Chiyoda-ku, Tokyo (JP)

(72) Inventors: Kiyoshi Fukada, Tokyo (JP); Hiroyuki Sumi, Tokyo (JP); Hidekazu Fujimoto, Tokyo (JP); Izumi Shimoyama, Tokyo (JP); Takashi Anyashiki, Tokyo (JP); Tetsuya Yamamoto, Tokyo (JP); Yusuke Dohi, Tokyo (JP)

(73) Assignee: JFE STEEL CORPORATION, Tokyo (JP)

( * ) Notice: Subject to any disclaimer, the term of this patent is extended or adjusted under 35 U.S.C. 154(b) by 597 days.

This patent is subject to a terminal disclaimer.

(21) Appl. No.: 14/387,734

(22) PCT Filed: Mar. 25, 2013

(86) PCT No.: PCT/JP2013/001980
§ 371 (c)(1),
(2) Date: Sep. 24, 2014

(87) PCT Pub. No.: WO2013/145678
PCT Pub. Date: Oct. 3, 2013

(65) Prior Publication Data
US 2015/0075961 A1 Mar. 19, 2015

(30) Foreign Application Priority Data
Mar. 27, 2012 (JP) ................................. 2012-071519

(51) Int. Cl.
*C10B 57/04* (2006.01)
*C10L 9/00* (2006.01)
(Continued)

(52) U.S. Cl.
CPC ................ *C10L 9/10* (2013.01); *C10B 57/04* (2013.01); *C10L 5/04* (2013.01); *C10L 9/00* (2013.01);
(Continued)

(58) Field of Classification Search
CPC .. C10B 57/04; C10L 2290/24; C10L 2290/60; C10L 2300/20; C10L 5/04; C10L 9/10; G01N 33/222
See application file for complete search history.

(56) References Cited

U.S. PATENT DOCUMENTS 9,463,980 B2 * 10/2016 Fukada ................... C10B 57/04
2013/0255142 A1 10/2013 Dohi

FOREIGN PATENT DOCUMENTS

JP 8-176553 A 7/1996
JP 09-255966 9/1997
(Continued)

OTHER PUBLICATIONS

Niekerk, et al., Blast-furnace coke: A coal-blending model, Journal of South African Inst. Min. Metall., 1991, vol. 91, No. 2, pp. 53-61.*
(Continued)

*Primary Examiner* — Renee Robinson
*Assistant Examiner* — Derek Mueller
(74) *Attorney, Agent, or Firm* — RatnerPrestia

(57) ABSTRACT

There is provided a method for blending coals for coke production, in which the strength of coke produced from a coal blend serving as a raw material is estimated using a physical property that has not been taken into consideration in the past as an index, so that the method is capable of suppressing an increase in the raw material cost of the coal blend and increasing the strength of coal. Two or more coal brands are blended together to provide a coal blend for coke production. When the two or more coal brands are blended
(Continued)

together, the coal brands and the blending ratio of the coal brands are determined using the surface tension of each of the coal brands subjected to heat treatment, the surface tension serving as a control index.

15 Claims, 5 Drawing Sheets

(51) Int. Cl.
    *C10L 9/10*     (2006.01)
    *G01N 33/22*     (2006.01)
    *C10L 5/04*     (2006.01)
    *G01N 13/00*     (2006.01)

(52) U.S. Cl.
    CPC ........... *G01N 13/00* (2013.01); *G01N 33/222* (2013.01); *C10L 2290/24* (2013.01); *C10L 2290/60* (2013.01); *C10L 2300/20* (2013.01)

(56) References Cited

FOREIGN PATENT DOCUMENTS

| JP | 2002-294250 A | 10/2002 |
|---|---|---|
| JP | 2005-281355 A | 10/2005 |
| JP | 2008069258 | 3/2008 |
| WO | 2012029983 | 3/2012 |

OTHER PUBLICATIONS

European Search Report dated Mar. 20, 2015 for European Application No. 13768167.2.
Forrest et al., "Theoretical and Experimental Approaches to the Carbonization of Coal and Coal Blends," Analytical Characterization Techniques, Nov. 12, 1982, vol. 205, pp. 1-25.
Oh et al., "An experimental and modeling study of softening coal pyrolysis," Aiche Journal, vol. 35, No. 5, May 1, 1989, pp. 775-792.
Dash et al,. "Laboratory scale investigation on maximising utilisation of carbonaceous inerts in stamp charging to improve coke quality and yield," Ironmaking & Steelmaking, vol. 34, No. 1, Jan. 1, 2007, pp. 23-29.
Korean Grant to Patent for KR2014-7027120 dated Feb. 29, 2016.
English Translation of Korean Grant to Patent for KR2014-7027120 dated Feb. 29, 2016.
R.P. Mather, "Investigation of the Heterogeneity of Organic Pigment Particle Surfaces Using a Film Flotation Method", Dyes and Pigments 43, pp. 47-50, 1999.
International Search Report dated May 7, 2013, application No. PCT/JP2013/001980.
J. K. Spelt and D. Li, "The equation of state approach to interfacial tensions, in Applied Surface Thermodynamics", A. W. Neumann and J. K. Spelt (Eds), Advances in Chemistry Series, vol. 63, Marcel Dekker, New York, 1996, p. 239-292.
D. W. Fuerstenau "International Journal of Mineral Processing", 20, 1987, p. 153.
Japanese Office Action with partial English language translation for Application No. 2014-507419, dated Dec. 24, 2014, 4 pages.

\* cited by examiner (A)

(a) (b)

(B)

(a) (b)

(C)

(a) (b)

METHOD FOR BLENDING COALS, AND METHOD FOR PRODUCING COKE

CROSS REFERENCE TO RELATED APPLICATIONS

This is the U.S. National Phase application of PCT/JP2013/001980, filed Mar. 25, 2013, which claims priority to Japanese Patent Application No. 2012-071519, filed Mar. 27, 2012, the disclosures of each of these applications being incorporated herein by reference in their entireties for all purposes.

FIELD OF THE INVENTION

The present invention relates to a method for blending coals, the coals serving as a raw material for blast furnace coke with high strength, a coal blend prepared by the blending method, and a method for producing coke from the coal blend.

BACKGROUND OF THE INVENTION

Blast furnace coke has been used as a reducing agent, a heat source, and a support to maintain gas permeability in a blast furnace. In recent years, there has been a trend toward the production of high-strength coke in order to achieve stable operation at a low reducing agent ratio. Upon producing blast furnace coke, a coal blend in which a plurality of coal brands (2 or more and 20 or less) are blended is commonly used. Thus, methods for predicting the strength of coke produced from the coal blend serving as a raw material has hitherto been studied. For example, the following methods described in items (i) to (iii) are known.

(i) Method for Predicting Strength of Coke Using Strength of Coke Matrix and Fluidity as Indices This method is a blending theory in which the strength of coke is predicted using two indices, i.e., the mean maximum reflectance of vitrinite (mean value of Ro) and Gieseler maximum fluidity (MF), as coal property parameters. Currently, the blending method is commonly employed.

(ii) Method for Predicting Strength of Coke Using NMR

This method is a method for predicting the strength of coke using an index indicating the amount of coal plastic component in coal measured by NMR (Nuclear Magnetic Resonance) and an index indicating the viscosity of the coal plastic component in coal (for example, see Patent Literature 1).

(iii) Method for Predicting Strength of Coke Using Blend Effect Coefficient as Index In common coke strength prediction expressions used in items (i), (ii), and so forth, the strength of coke produced by the carbonization of a coal blend in which a plurality of coal brands are blended is predicted by the weighted average of physical properties of coals blended. However, it is known that additivity does not hold between the strength of coke obtained from a single coal brand and the strength of coke obtained from a plurality of coal brands, in some cases. The reason the additivity does not hold is presumably due to the interaction between coal particles. In the coke strength prediction expressions in items (i) and (ii), the effect of increasing or decreasing the strength by the interaction, i.e., the blend effect, is often not considered. In contrast, the following is known: With respect to a method for predicting the blend effect, the coke properties of coke obtained from a coal blend including a plurality of coal brands are defined as coke properties of coke obtained from the set of combinations of two types of coal. The deviation of the coke properties from the weighted average of the coke properties of coke produced from a single coal brand is defined as a blend effect coefficient. A method for creating a coke strength prediction expression using the blend effect coefficient is employed (for example, see Patent Literature 2). The blend effect coefficient may be determined by actual measurement or prediction.

PATENT LITERATURE

PTL 1: Japanese Unexamined Patent Application Publication No. 2002-294250
PTL 2: Japanese Unexamined Patent Application Publication No. 9-255966

NON PATENT LITERATURE

NPL 1: J. K. Spelt and D. Li, "The equation of state approach to interfacial tensions, in Applied Surface Thermodynamics", A. W. Neumann and J. K. Spelt (Eds), Advances in Chemistry Series, vol. 63, Marcel Dekker, New York, 1996, p. 239-292
NPL 2: D. W. Fuerstenau "International Journal of Mineral Processing", 20, 1987, p. 153

SUMMARY OF THE INVENTION

While the foregoing methods are reported as a method for predicting the strength of coke in order to produce high-strength coke, the prediction accuracy of the strength of coke is not necessarily sufficient. One reason for the insufficient prediction accuracy is presumably that the influence of a factor in affecting the strength of coke, in particular, the interaction between coal particles, is not made clear. To produce high-strength coke by the method described in item (i), coal having high mean maximum reflectance of vitrinite (mean of Ro) and high maximum fluidity (MF) determined with a Gieseler plastometer is needed. Such coal is expensive, thus disadvantageously increasing the cost. In the case where non- or slightly-caking coal having poor fluidity is used, detection sensitivity to the index indicating the fluidity is reduced, thus disadvantageously causing difficulty in performing measurement and resulting in a meaningless measured value.

The method described in item (ii) utilizes the fluidity and viscosity of coal. In the end, an index with improved detection sensitivity to the maximum fluidity (MF) is used, thus disadvantageously increasing the cost in the same way as in item (i). Furthermore, the method is not a simple method with a complex measuring device, which is disadvantageous.

The method described in item (iii) utilizes the blend effect coefficient and thus can more accurately predict the strength of coke. After all, however, the method is not so different from a conventional method because the method utilizes parameters of a conventional coke strength expression; hence, the method does not solve the problem with cost. Although the interaction between coal particles is evaluated, the evaluation is not based on the physical properties relating to the adhesion of coal, leading to insufficient prediction accuracy of the strength. Thus, in the case where the blend effect coefficient is determined by actual measurement, the method is not convenient.

The present invention has been accomplished to overcome the foregoing problems. The present invention aims to provide a method for blending coals, in which the strength of coke produced from a coal blend serving as a raw material is predicted using a physical property that has not been taken into consideration in the past as an index, so that the method is capable of suppressing an increase in the raw material cost of the coal blend and increasing the strength of coal. The present invention also aims to provide a coal blend prepared by this blending method and a method for producing coke by carbonization of the coal blend.

The gist of the present invention to solve the foregoing problems is described below.

[1] A method for blending coals for coke production, the coals being prepared by blending two or more coal brands, the method comprising:

determining coal brands and blending ratio of the coal brands, by using surface tension of each of the coal brands subjected to heating to a temperature in the range of 350° C. to 800° C. and then cooling as a control index.

[2] The method for blending coals according to [1], comprising:

assuming the two or more coal brands and the blending ratio of the coals in advance, preparing surface tension distributions of the assumed two or more coal brands subjected to heating to a temperature in the range of 350° C. to 800° C. and then cooling, calculating a standard deviation ($\sigma 1$) of a distribution obtained by the weighted average of the prepared surface tension distributions, using the assumed blending ratio of the coals as a weighting factor, and using the standard deviation ($\sigma 1$) as the control index.

[3] The method for blending coals according to [2], wherein the surface tension distributions prepared are surface tension distributions of the coals subjected to heating to 500° C. and then cooling, the standard deviation ($\sigma 1$) is changed by changing the blending ratio of the coals assumed in advance, the blending ratio such that the changed standard deviation ($\sigma 1$) is 5.5 [mN/m] or less is defined as the blending ratio of the coals determined, and the coal brands assumed in advance are defined as the coal brands determined.

[4] The method for blending coals according to [1], wherein the coals blended are determined, and surface tension distributions of the respective coals are surface tension distributions of the coals subjected to heating to 500° C. and then cooling, and the blending ratio such that the standard deviation ($\sigma 1$) of a distribution obtained by the weighted average of the surface tension distributions is 5.5 [mN/m] or less is defined as the blending ratio of the coals determined.

[5] The method for blending coals according to [1], wherein the two or more coal brands and the blending ratio of the coals are assumed in advance, surface tension distributions of the assumed two or more coal brands subjected to heating to a temperature in the range of 350° C. to 800° C. and then cooling are prepared, the standard deviation ($\sigma 2$) of average values of the prepared surface tension distributions is calculated using the average values and the assumed blending ratio of the coals, and the standard deviation ($\sigma 2$) is used as the control index.

[6] The method for blending coals according to [5], wherein the surface tension distributions prepared are surface tension distributions of the coals subjected to heating to 500° C. and then cooling, the standard deviation ($\sigma 2$) is changed by changing the blending ratio of the coals assumed in advance, the blending ratio such that the changed standard deviation ($\sigma 2$) is 0.8 [mN/m] or less is defined as the blending ratio of the coals determined, and the coal brands assumed in advance are defined as the coal brands determined.

[7] The method for blending coals according to [1], wherein surface tension distributions of the respective colas blended are surface tension distributions of the coals subjected to heating to 500° C. and then cooling, and the blending ratio such that the standard deviation ($\sigma 2$) of average values of the surface tension distributions is 0.8 [mN/m] or less is defined as the blending ratio of the coals determined, the standard deviation ($\sigma 2$) being derived from the average values.

[8] The method for blending coals according to any one of [1] to [7], wherein the surface tension is measured by a film floatation method.

[9] A coal blend prepared by the method for blending coals according to any one of [1] to [8].

[10] A method for producing coke, comprising carbonizing the coal blend according to [9].

In the present invention, the coal brands included in a coal blend serving as a raw material for coke and the blending ratio of the coal brands are determined in consideration of the surface tension that affects the adhesive strength between coal particles. That is, the present invention relates to the interaction between coals (adhesion phenomenon), and coals are blended together using an index different from conventionally used indices. Furthermore, in the present invention, coals can be blended together under blending conditions using a new index, which cannot be conceived from conventional coal property parameters.

According to the present invention, coke is produced from a coal blend prepared by the foregoing blending, thereby increasing the estimation accuracy of a coke strength estimation expression. Furthermore, an increase in coal property parameter leads to a higher degree of flexibility in purchasing raw materials. This enables an increase in the strength of coke without increasing raw-material cost. The present invention may also be applied to low-fluidity non- or slightly-caking coal that is not readily evaluated with a Gieseler plastometer, thereby enhancing the degree of flexibility in blending coals.

DETAILED DESCRIPTION OF EMBODIMENTS OF THE INVENTION

Figure 1:
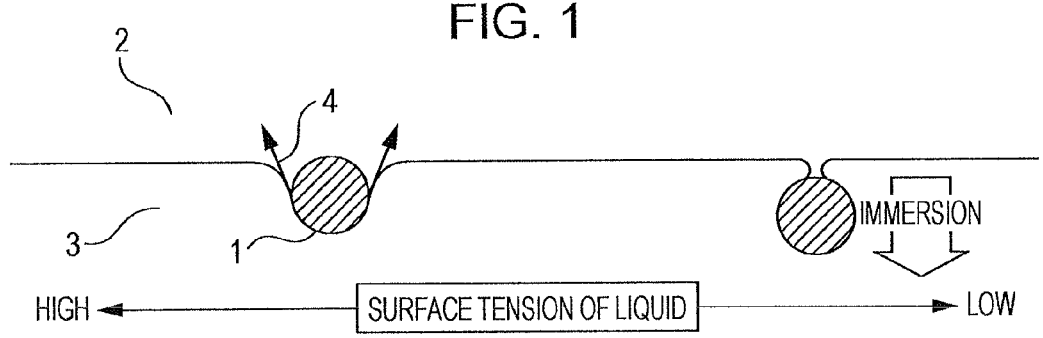
FIG. 1 illustrates the principle of surface tension measurement by a film floatation method.

Coal particles are softened and adhered together by carbonization, thereby producing coke. In consideration of the adherence phenomenon, the adhesive strength between coal particles affects the strength of coke. However, the facts that what physical property of coal affects the adhesive strength and that how much effect the physical property has on the strength of coke have been unknown. To reveal a physical property that affects the adhesive strength between coal particles and clarify the effect of the physical property on the strength of coke, the inventors have focused attention on the interfacial tension at the adhesive interface between coal particles as the physical property.

In general, a lower interfacial tension at the adhesive interface results in higher adhesive strength. The interfacial tension can be regarded as free energy present at the interface as indicated by being expressed in units of mN/m. The presence of the interfacial tension indicates that free energy that can act as force is present at the interface. In this case, a high interfacial tension may be liable to cause a break of the adhesive interface. A low interfacial tension may be less likely to cause a break of the adhesive interface. Based upon this speculation, the interfacial tension should be used for the prediction of the adhesive strength.

It is very difficult to measure the interfacial tension at the interface between coal particles of different coal brands by existing techniques. Thus, the inventors have employed a method for predicting interfacial tension on the basis of the surface tension of coal obtained by heat treatment of the coal brands described below (hereinafter, also referred to appropriately as "semi-coke"), instead of directly measuring the interfacial tension, and have conducted studies on a method for determining coal brands included in a coal blend and the blending ratio of the coal brands using the surface tension of the semi-coke. Hitherto, preferred surface tension measurement conditions for the purpose of predicting the strength of coke, a method for predicting interfacial tension from surface tension, the degree of influence on the strength of coke, and so forth have been unclear. The inventors have conducted studies on these unclear factors and have found an effective method for predicting the strength of coke. This finding has led to the completion of the present invention. Here, semi-coke refers to coal produced by heating coal to a temperature in the range of 350° C. to 800° C. and then cooling the coal, as described below.

Hereinafter, particulars relating to interfacial tension and surface tension, and a method for measuring surface tension when the particulars are applied to coal will first be described. According to the present invention, a method for blending coals using surface tension as an index and a method for producing coke will then be described.

Interfacial tension is expressed by the surface tensions of substances bonded together and is derived from the surface tension $\gamma_{AB}$ of the substances bonded together. The may be determined from surface tension $\gamma_A$ of substance A and surface tension $\gamma_B$ of substance B and is expressed by the following expression (1) using, for example, the Girifalco-Good equation (see Non-Patent Literature 1):

$$\gamma_{AB} = \gamma_A + \gamma_B - 2\phi(\gamma_A \gamma_B)^{0.5} \quad (1)$$

where φ represents an interaction coefficient (between substance A and substance B).

The interaction coefficient φ is 1 when the same substance is used. Although different coal brands are not the same substance, considering that the different coal brands are adhered together to form coke, we would say that the coals have relatively high wettability. Thus, the interaction coefficient φ is assumed to be a value close to 1. If the interaction coefficient φ is 1, the expression (1) can be transformed into the following expression (2):

$$\gamma_{AB} = (\gamma_A^{0.5} - \gamma_B^{0.5})^2 \quad (2)$$

Based on the expression (2), a larger difference in surface tension between two substances results in higher interfacial tension between the substances.

In the case where the foregoing general expressions relating to the interfacial tension of substances are applied to coal, items (A) and (B) regarding coal need to be studied.

(A) Coal is not a homogeneous substance. Even the same coal brand has locally different molecular structures and thus do not have the same surface tension.

(B) In a process of subjecting coal to carbonization into coke, a chemical change occurs, thus changing the physical properties, such as surface tension.

Thus, in the case where the effect of surface tension on the adhesive strength between coals is considered, the inventors needs to focus attention on a difference in surface tension between the coal brands used for a blend. Furthermore, the distribution of the surface tension and a change in surface tension due to heating need to be considered.

The adhesive strength between coal particles in the process of subjecting coal to carbonization into coke is seemingly affected by the surface tension of the coal for a period of time from when the softening of coal is initiated by heating to when the coal is converted into coke. Thus, the surface tension of coal in a softened state is preferably measured. However, it is difficult to measure the surface tension while coal is actually softened and adhered. The inventors have conducted studies and have found that the surface tension of coal in a softened state can be predicted by heating the coal to a temperature at which the coal is softened with air shut-off or in an inert gas atmosphere, cooling the coal in an inert gas atmosphere, and measuring the surface tension of the coal.

Based on the idea that adhesion between coal particles is affected by the surface tension, the heating temperature of coal is suitably set in a temperature range of a temperature at which the softening of the coal is initiated by heating to a temperature at which coking is completed by the adhesion and solidification of the coal, i.e., in a temperature range of 350° C. or higher, at which the softening is initiated, to 800° C., at which coking is completed. Thus, semi-coke is preferably produced by heating coal to 350° C. or higher with air shut-off or in an inert gas and then cooling the coal. Regarding the heating temperature in the range of 350° C. to 800° C., a temperature that particularly contributes to adhesion is a temperature at the time of softening. The temperature range of fluidity of coal used for the production of coke is 350° C. to 550° C. The bonded structure is seemingly determined at about 500° C. Thus, the heating temperature is particularly about 500° C. and preferably 480° C. to 520° C.

The reason the coal is cooled in the inert gas is to reduce the measurement error of the surface tension. The coal immediately after heating has a high temperature. Cooling the coal in an oxygen-containing atmosphere partially oxidizes the surface to cause the structure to change, leading to the measurement error of the surface tension. As the inert gas, a noble gas, for example, helium or argon gas, or nitrogen gas may be used. Usually, nitrogen gas may be used.

Preferably, the coal after heating is rapidly cooled. The reason the heated coal is rapidly cooled is to maintain a molecular structure in a softened state. The cooling is preferably performed at a cooling rate of 10° C./sec or more at which the molecular structure is seemingly unchanged. An example of a rapid cooling method is a method with liquid nitrogen, iced water, water, or an inert gas, such as nitrogen gas. Gas cooling takes a long time to cool the inside of the coal, thereby causing a cooling rate distribution. Cooling with iced water or water affects the measurement of the surface tension because of the adhesion of water. Thus, rapid cooling is preferably performed with liquid nitrogen. Specifically, a vessel that holds coal may be immersed in liquid nitrogen.

In the present invention, a method for heat-treating coal is described below.

(a) Coal is crushed. In this crushing of the coal, the coal is preferably crushed so as to have a particle size of 250 μm or less, which is a crushed particle size in the proximate analysis of coal according to JIS M8812.

(b) The coal crushed in step (a) is heated at an appropriate heating rate. This heating rate is preferably determined in response to a heating rate at which coke whose interfacial tension is evaluated is produced. The coal may be heated to a temperature in the range of 350° C. to 800° C. described above.

(c) The coal heated in step (b) is cooled with liquid nitrogen. In this cooling, preferably, the coal is rapidly cooled by the foregoing method.

Here, semi-coke is defined as coal obtained by performing heating to a temperature in the range of 350° C. to 800° C. and then performing cooling.

Known examples of a method for measuring surface tension include a sessile drop method, a capillary rise method, a maximum bubble pressure method, a pendant drop method, a drop-weight method, a plate method (Wilhelmy method), an advancing/receding contact method, a ring method, a tilting plate method, a retention time measurement method, and a film flotation method. Coal is composed of various molecular structures, so the surface tension of coal should be nonuniform. Thus, the film flotation method (see Non-Patent Literature 2) by which a surface tension distribution can be evaluated is particularly preferably employed.

The basic principle of the film floatation method is described with reference to FIG. 1. The film floatation method is a technique using the idea that when a crushed sample particle 1 is dropped from a gas phase 2 on a surface of a liquid 3 and then immersed in the liquid 3 (this is the case of a sample particle on the right-hand portion in FIG. 1, and when the contact angle is almost equal to 0°), the surface tension of the sample particle is equal to the surface tension of the liquid. Arrows 4 in FIG. 1 indicate the surface tension of the sample particle 1.

Figure 2:
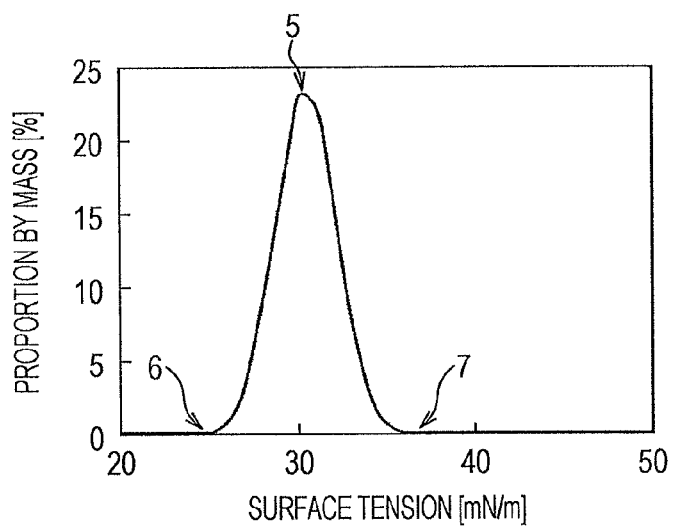
FIG. 2 is a frequency distribution curve illustrating the distribution of surface tension.

Sample particles are dropped on various liquids having different surface tensions. Proportions by mass of the sample particles floating on the liquids are determined. The results are expressed as a frequency distribution curve to obtain a surface tension distribution as illustrated in FIG. 2. Furthermore, the surface tension of a solid can be measured by the film floatation method. It is thus possible to measure the surface tension of any coal, for example, hard coking coal, non- or slightly-caking coal, or anthracite. Note that the surface tension directly determined by the film floatation method is critical surface tension (surface tension of a liquid at a contact angle of) 0°. It is possible to determine the surface tension of coal from the critical surface tension as described below.

Based on the foregoing expression (1), the surface tension $\gamma_L$ of a liquid, the surface tension $\gamma_S$ of a solid (coal or semi-coke), and the interfacial tension $\gamma_{SL}$ between the liquid and the solid satisfy the following relational expression:

$$\gamma_{SL} = \gamma_S + \gamma_L - 2\phi(\gamma_S \gamma_L)^{0.5} \quad (3)$$

where $\phi$ represents an interaction coefficient $\phi$ (of the solid and the liquid).

From Young's expression, the surface tension $\gamma_L$ of the liquid, the surface tension $\gamma_S$ of the solid (coal or semi-coke), and the interfacial tension $\gamma_{SL}$ between the liquid and the solid also satisfy the following relational expression:

$$\gamma_S = \gamma_L \cos\theta + \gamma_{SL} \quad (4)$$

where $\phi$ represents the contact angle of the solid to the liquid.

From the expressions (3) and (4), the following expression is derived:

$$1 + \cos\theta = 2\phi(\gamma_S/\gamma_L)^{0.5} \quad (5)$$

$\theta = 0°$, and $\gamma_L = \gamma_C$ ($\gamma_C$: critical surface tension) are substituted for the expression (5) to derive the following relational expression:

$$1 + 1 = 2\phi(\gamma_S/\gamma_C)^{0.5} \quad (6)$$

By raising the both sides of the expression (6) to the second power, the surface tension $\gamma_S$ of the solid and the critical surface tension $\gamma_C$ satisfy the following relation:

$$\phi^2 \gamma_S = \gamma_C \quad (7)$$

The surface tension $\gamma_S$ of coal or semi-coke can be determined from the expression (7) using the critical surface tension $\gamma_C$ and the interaction coefficient $\phi$.

There is a significant difference between the structure of a liquid used in the film floatation method and the structure of coal or semi-coke. A difference between structures of different coal brands is probably small, compared with the foregoing difference. The interaction coefficient $\phi$ is a parameter affected by their molecular structures. Given that the interaction coefficient $\phi$ is constant regardless of the coal brands, the surface tension $\gamma_S$ is expressed by the critical surface tension $\gamma_C$. Thus, we can say that the surface tension of coal or semi-coke is evaluated only by the critical surface tension.

As described above, the interaction coefficient (I) of coal or semi-coke is assumed to be close to 1. In the present invention, thus, the surface tension $\gamma_S$ of coal or semi-coke is assumed to be equal to the critical surface tension $\gamma_C$.

Requirements for the surface tension measurement by the film floatation method are described below. With respect to a liquid used in the film floatation method, coal has a surface tension ranging from 20 to 73 mN/m at normal temperature and during softening; hence, a liquid having a surface tension within the range may be used. For example, an organic solvent, for example, ethanol, methanol, propanol, tert-butanol, or acetone, is used. A liquid having a surface tension of 20 to 73 mN/m may be prepared from an aqueous solution of the organic solvent. With respect to the particle size of a sample subjected to surface tension measurement, the surface tension when the contact angle is substantially equal to 0° is desirably measured from the measurement principle described above. The contact angle increases as the particle size of the crushed sample particles increases. Thus, a smaller particles size is desirable. However, the sample particles having a particle size of less than 53 µm are easily aggregated. To prevent the aggregation, the sample particles are preferably crushed so as to have a particle size of 53 to 150 µm.

The film floatation method employs a floating phenomenon of a substance (sample particles) due to the surface tension, so the measurement needs to be performed under conditions where the gravity of a substance is negligible. The reason for this is that a substance having high density is affected by gravity to increase the contact angle. Thus, a substance having a density of 2000 kg/m$^3$ or less, in which gravity seemingly does not affect the contact angle, is desirably measured. Various types of coals and semi-cokes satisfy the requirement. A powder of any coal, for example, hard coking coal, non- or slightly-caking coal, or anthracite coal, or semi-coke may be used as sample particles used in the film floatation method. The surface tension may be measured by the method. Similarly, additives, such as pitch, oil coke, coke breeze, dust, waste plastics, and biomass, may also be measured.

Examples of steps in a method for processing coal to prepare a sample used in the film floatation method are described below.

(a') Coal is crushed so as to have a particle size of 200 µm or less.

(b') The coal crushed in step (a') is heated to 500° C. at a heating rate of 3° C./min in a stream of an inert gas. The heating rate in step (b') is set to 3° C./min so as to be matched with a heating rate when coke is produced in a coke oven.

(c') The coal heated in step (b') is rapidly cooled in liquid nitrogen.

(d') The coal rapidly cooled in step (c') is crushed so as to have a particle size of 150 µm or less. The crushed coal is dried at 120° C. for 2 hours in a stream of a dry inert gas. A drying method in step (d') may be any method by which water adhering on a surface is removed. Examples of the method that may be employed include a method in which coal is heated to 100° C. to 200° C. in an inert gas, for example, nitrogen or argon; and a method in which drying is performed under reduced pressure.

Examples of indices indicating surface tensions of single coal brand and semi-coke produced by the heat treatment of the single coal brand (hereinafter, appropriately referred to as "single-brand semi-coke") include an average value in a surface tension distribution (average surface tension), the standard deviation of the surface tension distribution, a surface tension at a peak in the surface tension distribution, two values of a maximum surface tension and a minimum surface tension in the surface tension distribution, and the distribution function of the surface tension distribution. The average value of the surface tension distribution (average value of $\gamma$) is expressed as, for example, expression (8) described below.

[Math. 1]

$$\bar{\gamma} = \int \gamma f(\gamma) d\gamma \quad (8)$$

where $\gamma$ with an overline represents the average value of a surface tension distribution, $\gamma$ represents a surface tension, $f(\gamma)$ represents the frequency of the surface tension distribution.

The standard deviation of a surface tension distribution ($\sigma_\gamma$) is expressed as, for example, expression (9) described below.

[Math. 2]

$$\sigma_\gamma = [\int (\gamma - \bar{\gamma})^2 f(\gamma) d\gamma]^{0.5} \quad (9)$$

Regarding a surface tension at a peak in the surface tension distribution, and a minimum surface tension and the maximum surface tension in the surface tension distribution, in a surface tension distribution illustrated in FIG. 2, reference numeral 5 denotes the peak value of the surface tension distribution. Reference numeral 6 denotes the minimum surface tension of the surface tension distribution. Reference numeral 7 denotes the maximum surface tension of the surface tension distribution. Regarding the distribution function of the surface tension distribution, distributions similar to the surface tension distribution in shape, for example, a normal distribution, a logarithmic normal distribution, an F distribution, a chi-square distribution, an exponential distribution, a gamma distribution, and a beta distribution, are exemplified.

After the foregoing description of the interfacial tension and the surface tension, the configuration of the present invention will be described. In the present invention, the standard deviation ($\sigma1$) of a distribution determined by the weighted average of surface tension distributions of single-brand semi-cokes produced from respective single coal brands, the blending ratio of each of the single coal brands in a coal blend being used as a weighting factor, and the standard deviation ($\sigma2$) of average values of the surface tension distributions of the respective single-brand semi-cokes, the standard deviation ($\sigma2$) being derived from the average values and the blending ratio of the single coal brands, are used as indices to predict the strength of coke produced from the coal blend. The reason the surface tension of the single-brand semi-cokes is measured instead of the single coal brands is as follows: Although the surface tension of coal correlates with the strength of coke and can be used to predict the strength of coke, the strength of coke correlates more with the surface tension of semi-coke than with the surface tension of coal. Thus, the surface tension of semi-coke is desirably used for the prediction of the strength of coke, compared with the surface tension of coal.

A method for blending coals according to the present invention includes steps described below.

Step (I): The brands of single coal brands and the blending ratio of the single coal brands are determined using the foregoing index, i.e., the surface tension of semi-coke, as a control index.

Step (II): Two or more coal brands are blended together on the basis of the coal brands and the blending ratio of the coals determined in the step (I).

A method for producing coke according to the present invention includes the steps (I) and (II) and further includes a step (III) of subjecting a coal blend prepared in the step (II) to carbonization.

The standard deviation ($\sigma1$) (first embodiment) or the standard deviation ($\sigma2$) (second embodiment) is preferably used as the control index. The inventors have found that the standard deviation ($\sigma1$) and the standard deviation ($\sigma2$) calculated from the surface tension of semi-coke correlate with the strength of coke produced by the carbonization of a coal blend and have accomplished the present invention using them as control indices.

First Embodiment

A method in which the standard deviation ($\sigma 1$) is used as a control index in the step (I) will be described. The step (I) preferably includes substeps (Ia) to (Id) described below.

Substep (Ia): The two or more coal brands included in a coal blend and the blending ratio of the coals are assumed, and a virtual coal blend is assumed.

Substep (Ib): The coals assumed in the substep (Ia) are heat-treated to produce semi-cokes, and surface tension distributions of the respective semi-cokes are prepared.

Substep (Ic): The surface tension distribution of virtual composite semi-coke that could be produced from the virtual coal blend is determined by the weighted average of the surface tension distributions prepared in the substep (Ib), the blending ratio of the coals assumed in the substep (Ia) being used as a weighting factor.

Substep (Id): The standard deviation ($\sigma 1$) of the virtual composite semi-coke determined in the substep (Ic) is used as a control index. In the case where the value of the control index is satisfactory, the coals assumed in the substep (Ia) is determined as coals blended in the step (II), and the blending ratio of the coals assumed in the substep (Ia) is determined as the blending ratio of the coals in the step (II).

The substeps (Ia) to (Id) will be described in detail below.

[Substep (Ia)]

Before the step (II) (in advance), the coal brands included in a coal blend are appropriately selected (assumed). Furthermore, the blending ratio of the coals is assumed, and a virtual coal blend is assumed. The case where the coal blend is composed of four coal brands will be described below.

[Substep (Ib)]

FIG. 3(a) illustrates surface tension distributions of four single-brand semi-cokes produced from four coal brands. Reference numeral 8 (8a, 8b, 8c, and 8d) represents a surface tension distribution curve of each of the single-brand semi-cokes. The preparation of the surface tension distributions includes the preparation of surface tension distributions obtained by measuring the surface tension of each of the single-brand semi-cokes by the film floatation method; the preparation of surface tension distributions on the basis of the surface tensions measured by a third party regardless of the film floatation method; and the acquisition of surface tension distributions from a third party.

Regarding the timing of the measurement of the surface tension of a single-brand semi-coke, it is desirable to perform the measurement immediately before the production of coke by the blending and carbonization of coals. The reason for this is that even in the case of the same brand of coal, property adjustment by a supplier of the coals and the degree of blending of the coals may result in a change in surface tension. The surface tensions are affected by the molecular structures of the coals. Thus, the measurement values of the surface tensions may be changed, depending on the state of preservation and weathering of the coals.

[Substep (Ic)]

A distribution is determined by the weighted average of the surface tension distributions of the semi-cokes produced from the coals, the blending ratio of the coals assumed in the substep (Ia) being used as a weighting factor. The distribution corresponds to the surface tension distribution of the virtual composite semi-coke that could be produced by the heat treatment of the virtual coal blend assumed in the substep (Ia). FIG. 3(b) illustrates the surface tension distribution of the virtual composite semi-coke, the distribution being determined from the surface tension distributions of the single-brand semi-cokes illustrated in FIG. 3(a). In the present invention, in the case where a blend of four single coal brands having different surface tension distributions is taken as an example, a distribution obtained by the weighted average of the frequencies of the surface tension distributions of the single-brand semi-cokes, the blending ratio of the single coal brands being used as a weighting factor, is interpreted as the surface tension distribution of the blended coal in a softened or molten state.

As described above, it is important to focus attention on the difference in surface tension in evaluating the adhesive strength. The surface tensions of coal and semi-coke have distributions. Thus, it is also important that the index indicating the surface tension appropriately express the breadth of the distribution of the surface tension. Hence, the standard deviation ($\sigma 1$) of the surface tension distribution of the virtual composite semi-coke is exemplified as a preferred control index. The standard deviation ($\sigma 1$) is determined by calculation if the surface tension of a single-brand semi-coke produced from a single coal brand can be known in advance, and thus may serve as an evaluation criterion for the surface tension distribution of a coal blend. Accordingly, the present invention is preferably applied to the case where a coal blend is prepared from a plurality of coal brands and where the strength of coke produced from the coal blend is estimated.

Given that the standard deviation ($\sigma 1$) is used as a control index and that a simple state is assumed, conditions such that the adhesive strength between coals in a coal blend is maximized are considered. Specifically, for example, assuming that the coal blend is composed of two coal brands and that the blending ratio of the coals is 1:1, let us discuss three cases: surface tension distributions of semi-cokes produced from the coals exhibit a relatively large difference (condition A), a relatively small difference (condition B), and are identical to each other (condition C). A necessary standard deviation ($\sigma 1$) for a virtual composite semi-coke in each case is considered.

Figure 4:
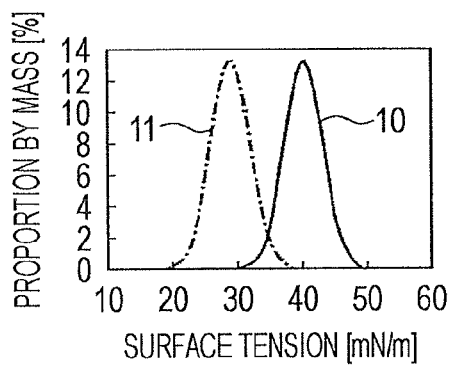
FIG. 4 illustrates the relationship between surface tension distributions of virtual composite semi-coke and standard deviations of the distributions.
Figure 4:
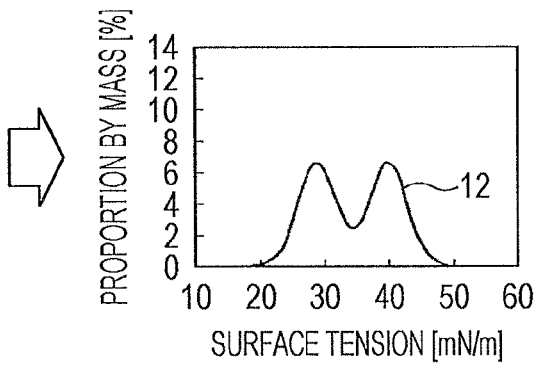
Figure 4:
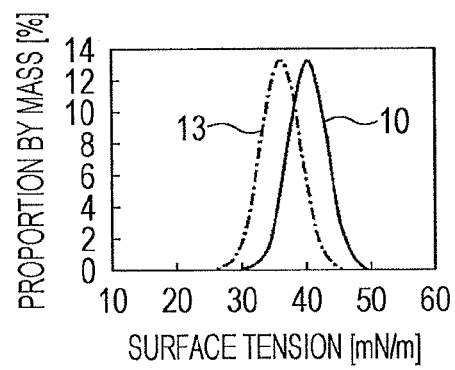
Figure 4:
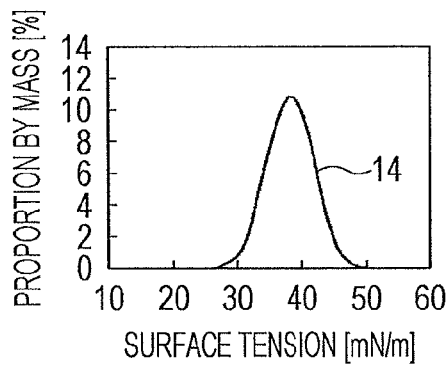
Figure 4:
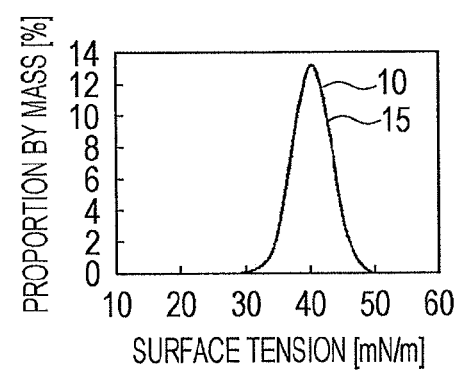
Figure 4:
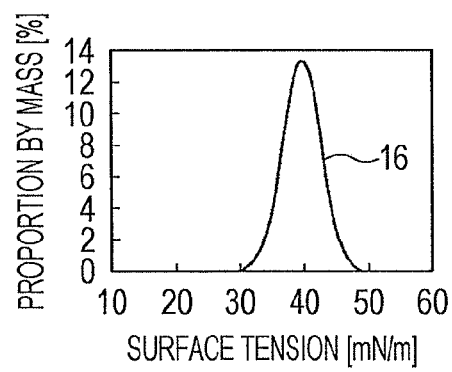

For the three cases, FIG. 4 illustrates surface tension distributions of single-brand semi-cokes and weighted average distributions of coal blends thereof. Graphs (a) in the left-hand side of FIG. 4 illustrate surface tension distributions of two semi-cokes under conditions A to C. Graphs (b) in the right-hand side of FIG. 4 illustrate schematic distributions obtained by the weighted average of the surface tension distributions of the two semi-cokes under the conditions at a weight ratio of 1:1. FIGS. 4(A) to (C) illustrate the cases under the conditions A to C.

Under the condition A, a surface tension distribution 10 of the semi-coke produced from coal x significantly differs from a surface tension distribution 11 of the semi-coke produced from coal a. A distribution 12 determined by the weighted average of these distributions has two peaks and is broad.

Under the condition B, a difference between the surface tension distribution 10 of the semi-coke produced from the coal x and a surface tension distribution 13 of semi-coke produced from coal b is smaller than that in the case of FIG. 4(A). The breadth of a distribution 14 determined by the weighted average of these distributions is relatively narrow.

Under the condition C, the surface tension distribution 10 of the semi-coke produced from the coal x is identical to a surface tension distribution 15 of semi-coke produced from coal c. The breadth of a distribution 16 determined by the weighted average of these distributions is smaller than that of the distribution 14 under the condition B.

As described above, regarding the breadth of the distributions determined by the weighted average, (condition A)>(condition B)>(condition C). Regarding the standard deviation (σ1) of these distributions, (condition A)>(condition B)>(condition C). In the case of a large breadth of the distribution, when coal particles included in a coal blend are in a softened state, the coal particles have a high probability of contact with particles having different surface tension. Thus, a large number of contact interfaces each having high interfacial tension and low adhesive strength occur in the coal blend in the softened state, thereby seemingly reducing the strength of coke produced from the coal blend. This demonstrates that the blending ratio of coals is desirably determined in such a manner that the breadth of the distribution determined by the weighted average of the surface tension distributions of the single-brand semi-cokes is small, i.e., the standard deviation (σ1) of the distribution is small.

[Substep (Id)]

In substep (Id), the standard deviation (σ1) of the surface tension distribution of the virtual composite semi-coke determined in the substep (Ic) is changed by changing the blending ratio of the coals assumed in the substep (Ia). The substeps (Ia) to (Ic) are performed once or multiple times to determine the blending ratio such that the standard deviation (σ1) is a predetermined value or less. The two or more coal brands assumed in the substep (Ia) and the determined blending ratio are determined as the brands of the single coal brands and the blending ratio of the single coal brands in the step (I).

In the substep (Ib), the semi-cokes are produced by heat treatment to 500° C. The substeps (Ia) to (Ic) are performed once or multiple times. The blending ratio such that the standard deviation (σ1) is 5.5 [mN/m] or less is preferably defined as the blending ratio of the coals determined. That is, the surface tension distributions prepared in the substep (Ib) are surface tension distributions of the semi-cokes produced by the heat treatment to 500° C. The blending ratio such that the standard deviation (σ1) calculated on the basis of the prepared surface tension distributions is 5.5 or less is preferably defined as the blending ratio of the coals determined. The standard deviation (σ1) may have a value and thus may be a value more than zero.

Modified First Embodiment

In this embodiment, the blending ratio of the single coal brands in the step (I) are determined using the fact that the standard deviation (σ1) calculated on the basis of the plural semi-cokes produced by the heat treatment to 500° C. is preferably 5.5 [mN/m] or less. In this embodiment, preferably, the step (I) further includes substeps (Ie) and (If) described below.

[Substep (Ie)]

First, two or more coal brands to be blended are determined. Semi-cokes produced from the coals are present. The semi-cokes exhibit distributions of surface tensions. The surface tension distributions correspond to the surface tension distributions of coals that have been subjected to heating to 500° C. and then cooling. The measurement of the surface tensions of the semi-cokes produced by the heat treatment of the coals is not necessarily required.

[Substep (If)]

The standard deviation (σ1) of a distribution is calculated, the distribution being determined by the weighted average of the surface tension distributions of the coals determined in the step (Ie). The blending ratio such that the standard deviation (σ1) is 5.5 [mN/m] or less is defined as the blending ratio of the coals determined. That is, in the substep (If), the blending ratio of the coals determined in the substep (Ie) is adjusted to an appropriate ratio. The standard deviation (σ1) of a distribution determined by the weighted average of surface tension distributions of semi-cokes produced from the determined coals is calculated, the appropriate ratio being used as a weighting factor. The blending ratio such that the standard deviation (σ1) is 5.5 [mN/m] or less is defined as the blending ratio of the single coal brands determined in the step (I). The coals determined in the substep (Ie) are defined as the single coal brands determined in the step (I).

Second Embodiment

A method for using the standard deviation (σ2) as a control index in the step (I) will be described. In the first embodiment, the standard deviation (σ1) is used as a control index. The substeps of calculating the standard deviation (σ1) are the substeps (Ic) and (Id). In the second embodiment, the substeps (Ia) and (Ib) other than those substeps are common to those in the first embodiment. substeps (Ic') and (Id') described below are preferably performed in place of the substeps (Ic) and (Id). In the following descriptions, explanations for portions common to the first embodiment are omitted.

In the step (I) of the second embodiment, after the substeps (Ia) and (Ib), the substeps (Ic') and (Id') described below are preferably performed.

Substep (Ic'): With respect to the plural surface tension distributions prepared in the substep (Ib), the average values of the respective surface tension distributions are calculated. The standard deviation (σ2) of the average values derived from the blending ratio of the coals assumed in substeps of (Ia) and the plural average values is determined. Note that the average values of the surface tension distributions of the semi-cokes obtained in the substep (Ib) indicate the average surface tensions of the semi-cokes.

Substep (Id'): The coal brands included in the coal blend and the blending ratio of the coals are determined using the standard deviation (σ2) determined in the substep (Ic') as a control index. The substeps (Ic') and (Id') will be described in detail below.

[Substep (Ic')]

Figure 3:
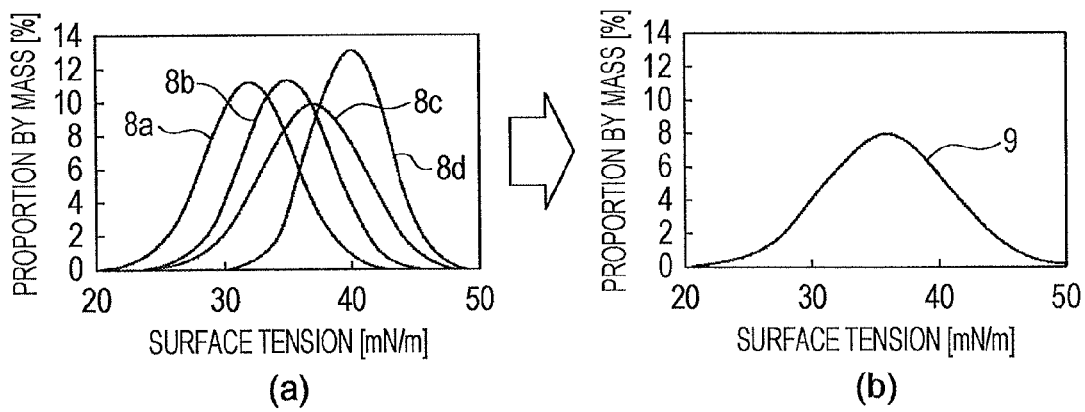
FIG. 3 illustrates conceptual drawings of surface tension distributions of virtual composite semi-coke.

Referring to the example illustrated in FIG. 3, the average values $\gamma_{8a}$, $\gamma_{8b}$, $\gamma_{8c}$, and $\gamma_{8d}$ of the surface tension distributions 8a, 8b, 8c, and 8d, respectively, in FIG. 3(a) are calculated. The standard deviation (σ2) is calculated from the resulting average values $\gamma_{8a}$, $\gamma_{8b}$, $\gamma_{8c}$, and $\gamma_{8d}$ and the blending ratio of the coals included in the coal blend, the coals being formed into the semi-cokes. Specifically, a coal blend is prepared from n-coal brands. Letting the average values of the surface tension distributions of the semi-cokes produced from the coals i of the n-brands be and letting the blending ratio be $w_i$, the standard deviation (σ2) is obtained as the square root of a dispersion and calculated from the following expression (10).

[Math. 3]

$$\sigma2 = \sqrt{\frac{\sum_{i}^{n} w_i \gamma_i^2}{\sum_{i}^{n} w_i} - \left(\frac{\sum_{i}^{n} w_i \gamma_i}{\sum_{i}^{n} w_i}\right)^2} \quad (10)$$

[Substep (Id')]

In the substep (Id'), the standard deviation ($\sigma 2$) determined in the substep (Ic') is changed by changing the blending ratio of the coals assumed in the substep (Ia). The substeps (Ia) to (Ic') are performed once or multiple times to determine the blending ratio such that the standard deviation ($\sigma 2$) is a predetermined value or less. The two or more coal brands assumed in the substep (Ia) and the determined blending ratio are determined as the brands of the coals and the blending ratio of the coals in the step (I).

In the case where the standard deviation ($\sigma 2$) is used as a control index, in the substep (Ib), the semi-cokes are produced by heat treatment to 500° C. The substeps (Ia) to (Ic') are performed once or multiple times. The blending ratio such that the standard deviation ($\sigma 2$) is 0.8 [mN/m] or less is preferably defined as the blending ratio of the coals determined. That is, the surface tension distributions prepared in the substep (Ib) are surface tension distributions of the semi-cokes produced by the heat treatment to 500° C. The blending ratio such that the standard deviation ($\sigma 2$) calculated on the basis of the prepared surface tension distributions is 0.8 or less is preferably defined as the blending ratio of the coals determined. The standard deviation ($\sigma 2$) may have a value and thus may be a value more than zero.

Modified Second Embodiment

In this embodiment, the blending ratio of the single coal brands in the step (I) are determined using the fact that the standard deviation ($\sigma 2$) calculated on the basis of the plural semi-cokes produced by the heat treatment to 500° C. is preferably 0.8 [mN/m] or less. In this embodiment, preferably, the step (I) further includes the substep (Ie) in the modified first embodiment and a substep (If') described below.

[Substep (If')]

The standard deviation ($\sigma 2$) of a distribution is calculated, the distribution being determined by the weighted average of the surface tension distributions of the coals determined in the step (Ie). The blending ratio such that the standard deviation ($\sigma 2$) is 0.8 [mN/m] or less is defined as the blending ratio of the coals determined. That is, in the substep (If'), the blending ratio of the coals determined in the substep (Ie) is adjusted to an appropriate ratio. The standard deviation ($\sigma 2$) of a distribution determined by the weighted average of surface tension distributions of semi-cokes produced from the determined coals is calculated, the appropriate ratio being used as a weighting factor. The blending ratio such that the standard deviation ($\sigma 2$) is 0.8 [mN/m] or less is defined as the blending ratio of the single coal brands determined in the step (I). The coals determined in the substep (Ie) are defined as the single coal brands determined in the step (I).

In summary, when the coals are blended together, the surface tension distributions of the coals or semi-cokes produced from the coals are measured. The surface tensions of the semi-cokes, for example, the standard deviation ($\sigma 1$) of the virtual composite semi-coke or the standard deviation ($\sigma 2$) of the average surface tension of the semi-cokes, are introduced as parameters of a coke strength prediction expression used for the control of blending. This results in improvement in the accuracy of the coke strength estimation expression. Furthermore, a coal that cannot be estimated by the use of conventional coal property parameters can also be evaluated, thereby improving the strength of coke. Moreover, the blend such that the standard deviation of the surface tension distribution is an optimum value is determined, thereby improving the strength of coke that cannot be predicted by the use of the conventional coal property parameters.

The inventors have conducted studies on a correlation between the surface tension of semi-coke produced from coal and the conventional coal property parameters and have found that there is no significant correlation between the surface tension and the mean maximum reflectance of vitrinite (mean of Ro), maximum fluidity (MF), a total inert content (TI), a distribution of mean reflectance ($\sigma$Ro), an ash content, results of elemental analysis, and so forth, which are used as the conventional coal property parameters. It can thus be said that the surface tension of semi-coke serves as an entirely new independent parameter.

The method according to the present invention may be applied not only to usual coal blending but also briquette blending. Furthermore, additives, such as non-caking coal, anthracite coal, pitch, oil coke, coke breeze, dust, waste plastics, and biomass, may be bonded to softened coal. Thus, when these substances are blended, the method according to the present invention may also be applied.

Example 1

Cokes were produced from single coal brands and coal blends. The strength of the cokes was measured. As the single coal brands, five coal brands (A to E) were used. Regarding the coal blends, two selected from the single coal brands were blended together in three blending ratios by mass of 75%:25%, 50%:50%, and 25%:75%. Combinations of the brands blended were selected in such a manner that different differences in surface tension between semi-cokes produced from the single coal brands are obtained.

Samples for the measurement of the surface tension when particles of the softened coals were bonded together were prepared as follows: Each coal was crushed so as to have a particle size of 200 μm or less. The crushed coal was charged into a graphite vessel and heated to 500° C. at 3° C./min with an electric furnace in an inert gas (nitrogen) atmosphere. Rapid cooling was performed by immersing the vessel in liquid nitrogen to produce semi-coke. The resulting semi-coke was crushed into 150 μm or less. The crushed semi-coke was dried at 120° C. for 2 hours in a stream of a dry inert gas.

The surface tension distribution of the resulting semi-coke was measured by the film floatation method. As a liquid used for the measurement of the surface tension by the film floatation method, ethanol and water, which are inexpensive and easily handled, were used.

As a control index, the standard deviation ($\sigma 1$) of the surface tension distribution of the virtual composite semi-coke was used. The standard deviation ($\sigma 1$) is a standard deviation (corresponding to the surface tension distribution of the virtual composite semi-coke) determined by the weighted average of the surface tension distributions of the single-brand semi-cokes, the blending ratio of the single-brand semi-cokes being used as a weighting factor.

The strength of coke was determined by a drum index test (DI 150/15). Regarding each of the five coal brands (A to E) and five types of coal blends (three blending ratios for each combination of the coals), 16 kg of coal was charged so as to have a bulk density of 750 kg/m$^3$, 100% by mass of the coal having a particle size of 3 mm or less, and the water content of the coal being adjusted to 8% by mass. The coal was subjected to carbonization in an electric furnace. After the carbonization at a furnace wall temperature of 1100° C.

for 6 hours, nitrogen cooling was performed. The drum index was measured. The drum index DI 150/15 is a drum index determined by charging coke into a predetermined drum, rotating the drum 150 turns at a rotation speed of 15 rpm, and then measuring the proportion by mass of coke having a particle size of 15 mm or more according to a drum strength test method specified by JIS K2151. The results of the drum index test and coal properties are summarized in Table 1.

TABLE 1

| Coal | Blending ratio (% by mass) | Ro (%) | logMF (logddpm) | TI (%) | σ1 (mN/m) | DI150/15 (—) |
|---|---|---|---|---|---|---|
| A | 100 | 0.71 | 1.32 | 37.8 | 6.32 | 71.8 |
| B | 100 | 0.84 | 3.11 | 17.5 | 5.25 | 76.1 |
| C | 100 | 0.93 | 2.56 | 34.3 | 4.22 | 74.4 |
| D | 100 | 1.07 | 2.09 | 37.4 | 3.88 | 79.2 |
| E | 100 | 1.62 | 1.28 | 23.4 | 3.83 | 80.8 |
| A-C | 75:25 | 0.76 | 1.63 | 36.9 | 6.16 | 75.8 |
|  | 50:50 | 0.82 | 1.94 | 36.1 | 5.82 | 76.8 |
|  | 25:75 | 0.87 | 2.25 | 35.2 | 4.69 | 75.4 |
| A-E | 75:25 | 0.94 | 1.31 | 34.2 | 6.10 | 77.5 |
|  | 50:50 | 1.17 | 1.30 | 30.6 | 5.79 | 80.0 |
|  | 25:75 | 1.39 | 1.29 | 27.0 | 4.42 | 82.3 |
| B-C | 75:25 | 0.86 | 2.97 | 21.7 | 5.05 | 79.4 |
|  | 50:50 | 0.88 | 2.83 | 25.9 | 4.83 | 77.1 |
|  | 25:75 | 0.90 | 2.69 | 30.1 | 4.55 | 78.0 |
| B-D | 75:25 | 0.90 | 2.86 | 22.5 | 5.30 | 80.1 |
|  | 50:50 | 0.96 | 2.60 | 27.5 | 4.96 | 79.2 |
|  | 25:75 | 1.01 | 2.34 | 32.4 | 4.69 | 79.0 |
| C-D | 75:25 | 0.96 | 2.44 | 35.1 | 4.41 | 77.1 |
|  | 50:50 | 1.00 | 2.32 | 35.9 | 4.19 | 76.9 |
|  | 25:75 | 1.03 | 2.20 | 36.6 | 4.23 | 79.0 |

The conventional coke strength estimation expression was derived as described below.

Three properties, the mean maximum reflectance of vitrinite (mean of Ro), Gieseler maximum fluidity (log MF), and a total inert (TI) content, are employed as parameters of the conventional coke strength estimation expression.

Regarding the coal blends each composed of the combination of the two coal brands described in Table 1, values calculated by the weighted average of the properties of the single coal brands described in Table 1 are defined as typical values of the properties of the coal blends, the blending ratio of the coals being used as a weighting factor.

The typical values of the three properties of each of the coal blends and the measurement value of the drum index were subjected to multiple regression analysis to derive a coke strength prediction expression for estimating the drum index using the typical values of the three properties of each coal blend as independent variables. Note that Ro and TI were measured in conformity with JIS M8816 and that MF was measured in conformity with JIS M8801.

Regarding a coke strength estimation expression according to the present invention, Ro, log MF, and TI described above were used as the conventional parameters, and the standard deviation (σ1) was added as a new parameter. As with the derivation of the conventional coke strength estimation expression, multiple regression analysis was performed to derive the coke strength estimation expression.

Figure 5:
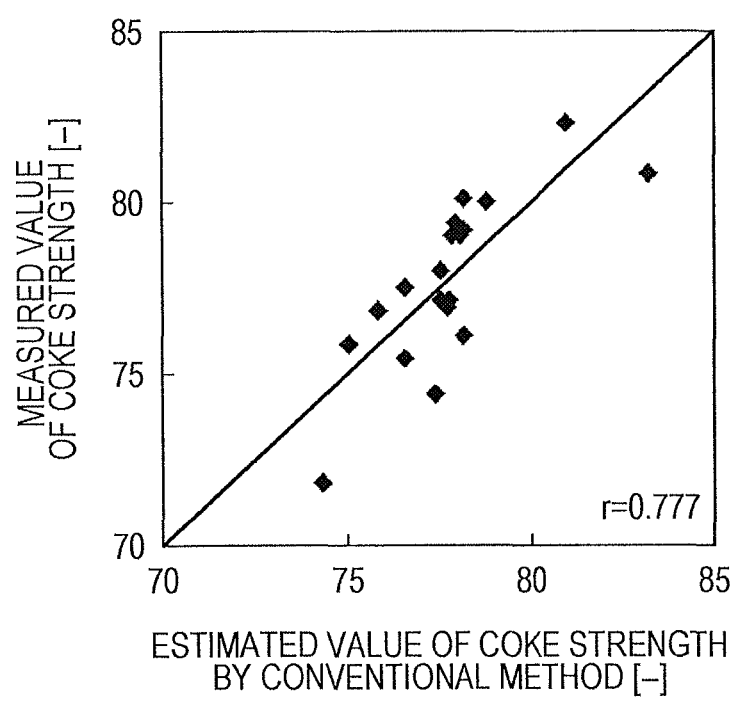
FIG. 5 is a graph illustrating the regression results of drum index values estimated by a conventional coke strength prediction method and observed drum index.
Figure 6:
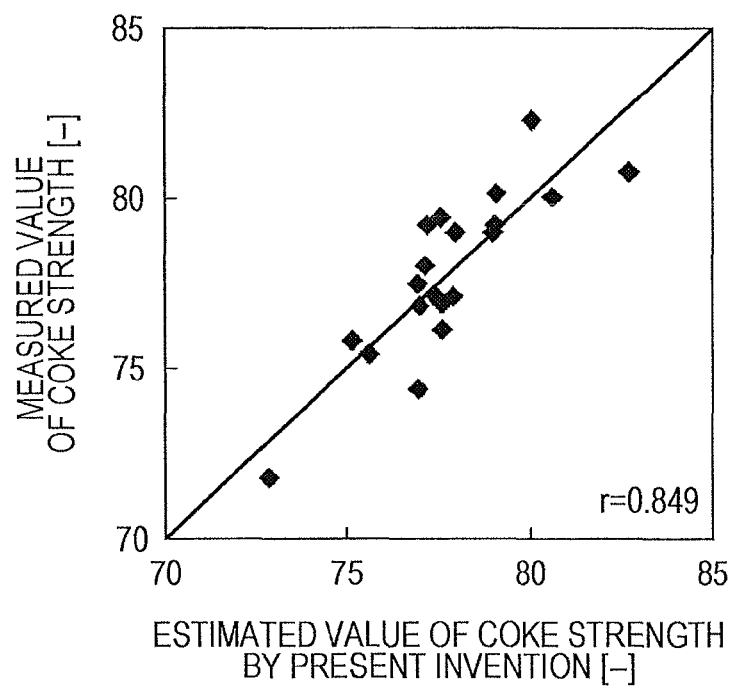
FIG. 6 is a graph illustrating the regression results of drum index values estimated by a coke strength estimation method according to the present invention and observed drum index.

FIG. 5 illustrates the relationship between the estimated value by the conventional coke strength estimation expression and the measured strength. FIG. 6 illustrates the relationship between the estimated value by the coke strength prediction expression according to the present invention and the measured strength.

The correlation coefficient between the estimation value and the measured value of the strength of coke in FIG. 5 was 0.777. The correlation coefficient between the prediction value and the measured value of the strength of coke in FIG. 6 was 0.849. The results revealed that the accuracy of the coke strength prediction expression is improved by measuring the surface tension of coal and using the surface tension as an index, thereby enabling the production of high-strength coke that cannot be predicted by the conventional coal property parameters.

Example 2

Next, the relationship between the breadth of a surface tension distribution and the strength of coke were studied. Four types of coal blends (blend A to D) were prepared with 13 coal brands (F to R), the coal blends being substantially the same in terms of Ro and log MF and being different in terms of the standard deviation (σ1) and the standard deviation (σ2). Table 2 describes the properties of the coals, the blending ratio of the coals (% by mass on a dry basis), and the strength of cokes produced by the carbonization of the coal blends, which were determined in the same ways as in Example 1.

TABLE 2

| Brand of coal | Ro [—] | logMF [logddpm] | γ [mN/m] | Blending ratio [%] | | | |
|---|---|---|---|---|---|---|---|
|  |  |  |  | Blend A | Blend B | Blend C | Blend D |
| Coal F | 1.29 | 1.04 | 40.6 | 28 | 18 | 12 | 12 |
| Coal G | 0.76 | 2.21 | 40.2 | 0 | 8 | 12 | 3 |
| Coal H | 0.68 | 4.11 | 41.1 | 6.5 | 0 | 0 | 0 |
| Coal I | 0.75 | 1.82 | 40.6 | 8.5 | 0 | 0 | 0 |
| Coal J | 0.99 | 1.15 | 40.9 | 0 | 9 | 0 | 0 |
| Coal K | 0.98 | 2.88 | 40.2 | 17 | 0 | 0 | 0 |
| Coal L | 0.82 | 4.43 | 39.9 | 0 | 0 | 3 | 5 |
| Coal M | 0.98 | 3.08 | 39.6 | 0 | 5 | 20 | 20 |
| Coal N | 0.85 | 3.13 | 40.9 | 20 | 30 | 0 | 30 |
| Coal O | 0.89 | 3.59 | 39.1 | 0 | 0 | 23 | 0 |
| Coal P | 1.07 | 3.18 | 39.7 | 20 | 0 | 0 | 0 |
| Coal Q | 1.10 | 2.03 | 38.9 | 0 | 30 | 0 | 0 |
| Coal R | 1.15 | 1.49 | 37.6 | 0 | 0 | 30 | 30 |
| Ro of coal blend [%] |  |  |  | 1.01 | 1.01 | 1.01 | 1.01 |
| log MF of coal blend [log ddpm] |  |  |  | 2.35 | 2.36 | 2.35 | 2.35 |
| Standard deviation (σ1) [mN/m] |  |  |  | 4.69 | 5.52 | 5.71 | 5.81 |
| Standard deviation (σ2) [mN/m] |  |  |  | 0.45 | 0.87 | 1.09 | 1.37 |
| Strength of coke DI150/15 [—] |  |  |  | 81.9 | 82.2 | 81.4 | 80.4 |
| Strength of coke CSR [%] |  |  |  | 64.1 | 64.5 | 63.4 | 59.7 |

In Table 2, Ro and log MF of the coal blends are average values determined by the weighted average of the properties of the single coal brands, the blending ratio of the single coal brands being used as a weighting factor. In Table 2, the standard deviations (σ1) are the standard deviations of distributions determined by the weighted average of the surface tension distributions of semi-cokes produced from the coals, the blending ratio of the coals being used as a weighting factor. The semi-cokes are produced by heating the coals to 500° C. and then cooling the coals. In Table 2, the standard deviations (σ2) are standard deviations determined from the expression (10) using the average values of surface tension distributions of semi-cokes produced from the coals and the blending ratios of the coals. Note that CSR represents the strength of cokes after reaction in $CO_2$ in conformity with ISO 18894.

Figure 7:
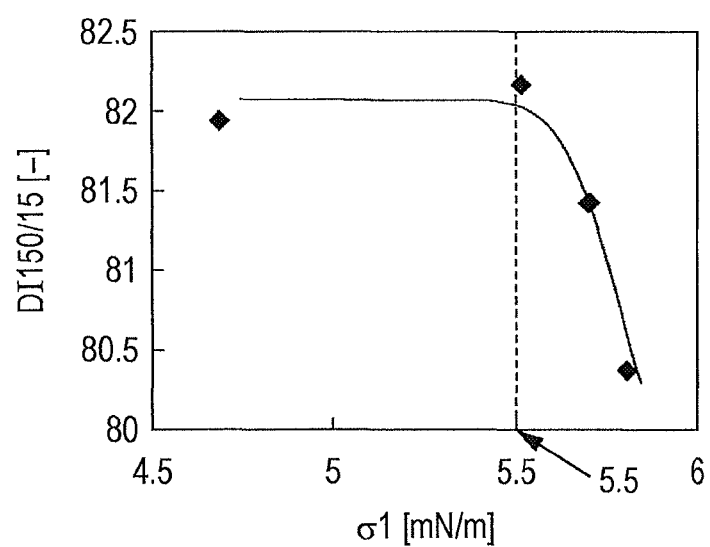
FIG. 7 is a graph illustrating the relationship between the strength of coke and the standard deviation ($\sigma 1$) of a distribution determined by the weighted average of surface tension distributions of semi-cokes produced by the heat treatment of the coal brands included in a coal blend, the blending ratio of each of the coals being used as a weighting factor.
Figure 8:
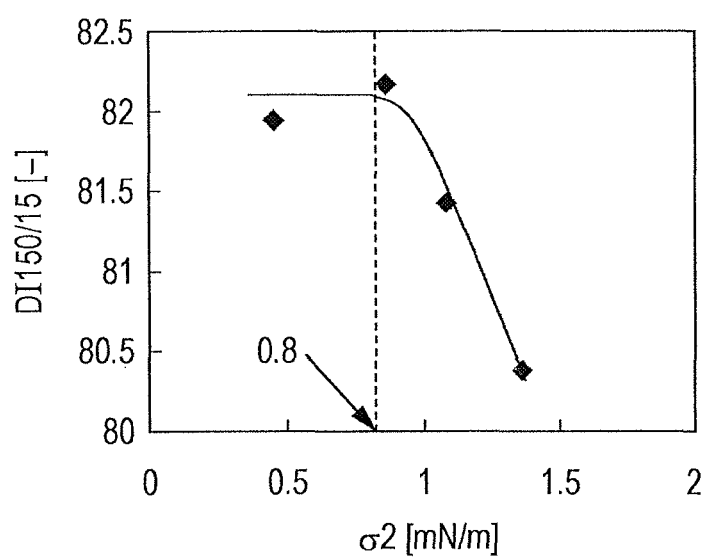
FIG. 8 is a graph illustrating the relationship between the strength of coke and the standard deviation (σ2) of the average of surface tension distributions of semi-cokes produced by the heat treatment of the coal brands included in a coal blend.

FIG. 7 illustrates the relationship between the strength of coke DI 150/15 and the standard deviation (σ1). FIG. 8 illustrates the relationship between the strength of coke DI 150/15 and the standard deviation (σ2). FIGS. 7 and 8 reveal that the broadening of the surface tension distribution (increase in standard deviation (σ1 and σ2)) results in a reduction in the strength of coke. In these coal blends, mean Ro and log MF of the coal blends were adjusted to be constant; hence, the strength of cokes are presumed to be similar values on the basis of a conventional blending theory. However, the results of this example demonstrate that the surface tension and its distribution affect the strength of coke in addition to the conventional parameters. The results also reveal that when the surface tension distribution σ is a certain value or less, the strength of coke is less affected. For example, the standard deviation (σ1) is preferably 5.5 [mN/m] or less, and the standard deviation (σ2) is preferably 0.8 [mN/m] or less.

The fact that the strength of coke is less likely to be affected at a standard deviation (σ1 or σ2) of a certain value or less can be estimated because even semi-coke produced from single coal brand exhibits a certain degree of surface tension distribution. That is, the surface tension distribution of the virtual composite semi-coke is not narrower than the surface tension distribution of semi-coke produced from single coal brand. Thus, the lower limit of the standard deviation σ1 is a minimum value of the standard deviation of the surface tension distribution of single-brand semi-coke. When the standard deviation σ1 is closer to the lower limit, the surface tension distribution of the virtual composite semi-coke will have a less effect on the strength of coke. At a lower standard deviation σ2, the distribution is closer to the surface tension distribution of semi-coke produced from single coal brand. Thus, the surface tension distribution of the virtual composite semi-coke will have a less effect on the strength of coke.

Surface tension distributions of semi-cokes produced from coals used for the production of cokes are measured. In the case where the plural coal brands are blended together, the coal brands and the blending ratio are determined in such a manner that the standard deviation (σ1) of the surface tension distribution of virtual composite semi-coke composed of a plurality of semi-cokes and the standard deviation (σ2) of the average surface tension of the plural semi-cokes are certain values or less, thereby preparing a coal blend serving as a raw material for high-strength coke.

Example 3

Semi-cokes were produced from coal S and coal T at different heat-treatment temperatures in the same way as in Example 1, and their surface tensions were measured. Table 3 describes the results.

TABLE 3

| | Heat treatment temperature (° C.) | | | | | |
|---|---|---|---|---|---|---|
| | 350 | 400 | 450 | 500 | 600 | 800 |
| Surface tension of semi-coke from coal S [mN/m] | 31.9 | 33.0 | 35.5 | 41.1 | 45.2 | 52.3 |
| Surface tension of semi-coke from coal T [mN/m] | 29.8 | 30.4 | 32.4 | 37.6 | 42.2 | 48.7 |

As is clear from Table 3, in a temperature range of 350° C. or higher, a higher heat-treatment temperature has a tendency to cause an increase in surface tension. However, the difference in surface tension between the two semi-cokes obtained at the same heat-treatment temperature was substantially constant. The magnitude relationship between the surface tensions of the different coals was not changed at different temperatures at which the semi-cokes were prepared. Although a higher heat-treatment temperature had a tendency to cause the surface tension distributions to broaden slightly, the surface tension distributions were not significantly changed.

Accordingly, the method according to the present invention is particularly effective when the heat-treatment temperature for the preparation of semi-coke is in the range of 350° C. to 800° C. because a possible temperature at which coal begins to soften is 350° C. In view of the dependence of the surface tension on the heat-treatment temperature, preferably, all coals blended are treated at substantially the same heat-treatment temperature, and the surface tensions thereof are evaluated.

REFERENCE SIGNS LIST 1 sample particle
2 gas phase
3 liquid
4 surface tension
5 peak value of surface tension distribution
6 minimum surface tension of surface tension distribution
7 maximum surface tension of surface tension distribution
8 (8a, 8b, 8c, 8d) surface tension distribution curve of single-brand semi-coke
9 distribution curve obtained by weighted average of surface tension distributions of single-brand semi-cokes using blending ratio as weighting factor
10 surface tension distribution of semi-coke produced from coal x
11 surface tension distribution of semi-coke produced from coal a
12 distribution obtained by weighted average of surface tension distributions 10 and 11
13 surface tension distribution of semi-coke produced from coal b
14 distribution obtained by weighted average of surface tension distributions 10 and 13
15 surface tension distribution of semi-coke produced from coal c
16 distribution obtained by weighted average of surface tension distributions 10 and 15

The invention claimed is:

1. A method for blending coals for coke production, the method comprising:
   a) determining surface tensions for semi-cokes prepared from each of a plurality of coals by heating the coals to a temperature in a range of 350° C. to 800° C. and then cooling;
   b) setting the relative amounts of two or more coals selected from said plurality of coals, based on surface tension data from the corresponding semi-cokes; and
   c) blending the two or more coals.

2. The method according to claim 1, wherein said setting in step b) comprises
   b1) selecting a virtual blend in which the two or more coals and their relative amounts are predetermined;
   b2) calculating the standard deviation σ1 of a distribution that is the weighted average of surface tension distributions determined for the semi-cokes corresponding to each of the coals in the virtual blend, weighted according to the relative amounts of the coals therein; and
   b3) if σ1 does not exceed a predetermined value, setting the relative amounts of the two or more coals to be those of the virtual blend, and otherwise adjusting the relative amounts of the two or more coals such that the predetermined value of σ1 is not exceeded and setting the relative amounts to the adjusted values.

3. The method according to claim 2, wherein the heating is performed at 500° C. and the predetermined value of σ1 is 5.5 mN/m.

4. The method according to claim 1,
wherein the two or more coals are predetermined, the heating is performed at 500° C., and said setting in step b) comprises selecting the relative amounts of the two or more coals such that σ1 is 5.5 mN/m or less, wherein σ1 is the standard deviation of a distribution that is the weighted average of surface tension distributions determined for the semi-cokes corresponding to each of the two or more coals, weighted according to the relative amounts thereof to be blended.

5. The method according to claim 1,
wherein said setting in step b) comprises
b1) selecting a virtual blend in which the two or more coals and their relative amounts are predetermined;
b2) calculating the standard deviation σ2 of average surface tensions obtained from the surface tension distributions determined for the semi-cokes corresponding to the coals in the virtual blend, weighted according to the relative amounts of the coals therein; and
b3) if σ2 does not exceed a predetermined value, setting the relative amounts of the two or more coals to be those of the virtual blend, and otherwise adjusting the relative amounts of the two or more coals such that the predetermined value of σ2 is not exceeded and setting the relative amounts to the adjusted values.

6. The method according to claim 5,
wherein the heating is performed at 500° C. and the predetermined value of σ2 is 0.8 mN/m.

7. The method according to claim 1,
wherein the heating is performed at 500° C., and said setting in step b) comprises selecting the relative amounts of the two or more coals such that σ2 is 0.8 mN/m or less, wherein σ2 is the standard deviation of average surface tensions obtained from the surface tension distributions determined for the semi-cokes corresponding to the two or more coals, weighted according to the relative amounts thereof to be blended.

8. The method according to claim 1, wherein the surface tension data are measured by a film floatation method.

9. The method according to claim 2, wherein the surface tension data are measured by a film floatation method.

10. The method according to claim 3, wherein the surface tension data are measured by a film floatation method.

11. The method according to claim 4, wherein the surface tension data are measured by a film floatation method.

12. The method according to claim 5, wherein the surface tension data are measured by a film floatation method.

13. The method according to claim 6, wherein the surface tension data are measured by a film floatation method.

14. The method according to claim 7, wherein the surface tension data are measured by a film floatation method.

15. A method for producing coke, comprising carbonizing a coal blend prepared by the method for blending coals according to claim 1.

* * * * *